United States Patent
Asaka et al.

Patent Number: 5,631,355
Date of Patent: May 20, 1997

[54] 5-O-DESOSAMINYLERYTHRONOLIDE A DERIVATIVES

[75] Inventors: Toshifumi Asaka; Masato Kashimura; Yoko Misawa; Shigeo Morimoto; Katsuo Hatayama, all of Tokyo, Japan

[73] Assignee: Taisho Pharmaceutical Co., Ltd., Japan

[21] Appl. No.: 318,862

[22] PCT Filed: Apr. 21, 1993

[86] PCT No.: PCT/JP93/00517

§ 371 Date: Oct. 17, 1994

§ 102(e) Date: Oct. 17, 1994

[87] PCT Pub. No.: WO93/21200

PCT Pub. Date: Oct. 28, 1993

[30] Foreign Application Priority Data

Apr. 22, 1992 [JP] Japan .................................. 4-101492

[51] Int. Cl.$^6$ .................................................. C07H 17/08
[52] U.S. Cl. .................................. 536/7.4; 536/7.2
[58] Field of Search ........................... 536/7.2, 7.4

[56] References Cited

U.S. PATENT DOCUMENTS

| | | | |
|---|---|---|---|
| 4,742,049 | 5/1988 | Baker et al. | 514/29 |
| 5,175,150 | 12/1992 | Omura et al. | 514/29 |
| 5,403,923 | 4/1995 | Kashimura et al. | 536/7.4 |
| 5,444,051 | 8/1995 | Agouridas et al. | 536/7.2 |

FOREIGN PATENT DOCUMENTS

| | | |
|---|---|---|
| 0559896 | 11/1991 | European Pat. Off. . |
| 0487411 | 11/1991 | European Pat. Off. . |
| 0559896 | 9/1993 | European Pat. Off. . |
| 62-292795 | 12/1987 | Japan . |
| 9209614 | 6/1992 | WIPO . |
| 9313116 | 7/1993 | WIPO . |
| 9313115 | 7/1993 | WIPO . |

OTHER PUBLICATIONS

Antimicrobial Agents & Chemotherapy, vol. 6, No. 4 pp. 479–488 (1974).
Journal of Medicinal Chemistry, vol. 17, No. 9 pp. 953–956 (1974).

*Primary Examiner*—Elli Peselev
*Attorney, Agent, or Firm*—Lorusso & Loud

[57] ABSTRACT

Object: To provide novel macrolide antibiotics having a strong antibacterial activity. Constitution: 5-O-desosaminylerythronolide A derivatives represented by the formula:

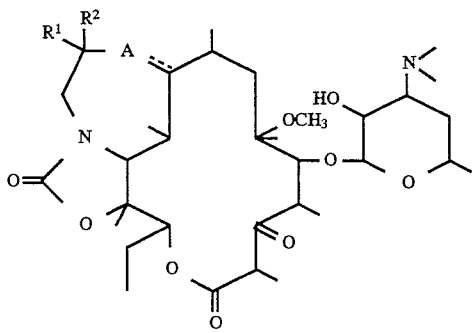

[wherein -A-_-_ is a group of —N($R^3$)— (wherein $R^3$ is a hydrogen atom or an alkyl group having 1–3 carbon atoms) or a group represented by —N==, and $R^1$ and $R^2$ are each a hydrogen atom or an alkyl group having 1–3 carbon atoms] which is a tricyclic carbamate of 5-O-desosaminylerythronolide A derivative having a ketone at the 3-position, being substituted by a methoxy group at the 6-position, and a pharmaceutically acceptable acid addition salt thereof; and a compound represented by the formula:

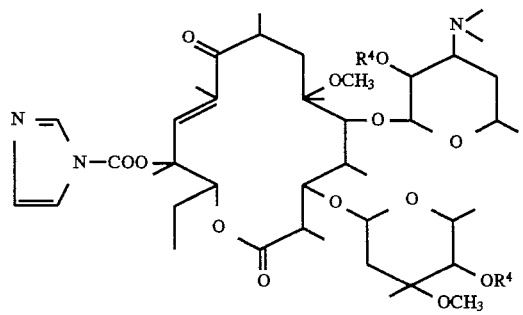

(wherein $R^4$ is an acetyl group or a propionyl group) which is an intermediate useful for the preparation of the 3-ketone forms of 5-O-desosaminylerythronolide A derivatives.

1 Claim, No Drawings

5-O-DESOSAMINYLERYTHRONOLIDE A DERIVATIVES

TECHNICAL FIELD

The present invention relates to novel derivatives of an antibiotic erythromycin, and more particularly relates to novel 5-O-desosaminyl-erythronolide A derivatives, pharmaceutically acceptable acid addition salts thereof and intermediates for the preparation thereof.

BACKGROUND OF ART

Erythromycins are antibiotics clinically widely used as agents for treating infectious diseases caused by Gram-positive bacteria, some Gram-negative bacteria, mycoplasmas, etc. Many erythromycin derivatives have been prepared for the improvement of biological and/or pharmaceutical properties of erythromycins. Certain ketone forms at the 3-position of 5-O-desosaminylerythronolide A have been described in Antimicrobial Agents and Chemotherapy, vol. 6, No. 4, page 479 (1974) and Journal of Medicinal Chemistry, vol. 17, No. 9, page 953 (1974), but generally they have extremely weak antibacterial activity. An object of the present invention is to provide novel antibiotics having a strong antibacterial activity.

DISCLOSURE OF THE INVENTION

As a result of various researches on the antibacterial activity of 3-ketone forms of 5-O-desosaminylerythronolide A derivatives, the present inventors have found that tricyclic carbamates substituted by a methoxy group at the 6-position have a strong antibacterial activity, and the present invention has been accomplished.

The present invention relates to 5-O desosaminylerythronolide A derivatives represented by the formula:

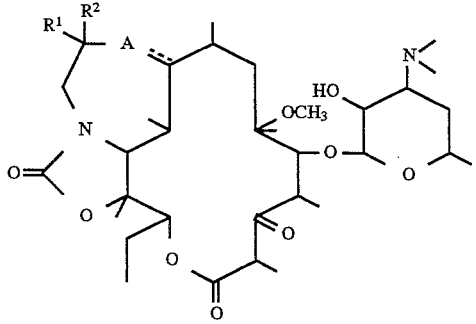

[wherein -A-- is a group of —N($R^3$)— (wherein $R^3$ is a hydrogen atom or an alkyl group having 1–3 carbon atoms) or a group represented by —N=, and $R^1$ and $R^2$ are each a hydrogen atom or an alkyl group having 1–3 carbon atoms], and a pharmaceutically acceptable acid addition salt thereof, and a 10,11-anhydro-12-O-imidazolylcarbonyl-6-O-methylerythromycin A protected by the same acyl groups at the 2'- and 4"-positions represented by the formula:

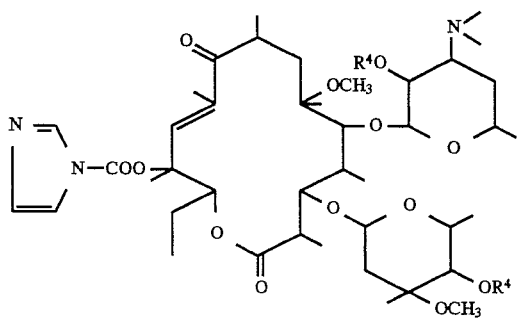

(wherein $R^4$ is an acetyl group or a propionyl group) which is a useful intermediate for the preparation of the 3-ketone form of 5-O-desosaminylerythronolide A derivatives.

In the present invention, the alkyl group having 1–3 carbon atoms is one which is a straight or branched chain. The pharmaceutically acceptable acid addition salt means, for example, acetate, propionate, butyrate, formate, trifluoroacetate, maleate, tartrate, citrate, stearate, succinate, ethylsuccinate, lactobionate, gluconate, glucoheptonate, benzoate, methanesulfonate, ethanesulfonate, 2-hydroxyethane-sulfonate, benzenesulfonate, p-toluenesulfonate, laurylsulfate, malate, aspartate, glutaminate, adipate, cysteine salt, hydrochloride, hydrobromide, phosphate, sulfate, hydroiodide, nicotinate, oxalate, picrate, thiocyanate, undecanoate, polyacrylate or carboxyvinyl polymer salt.

The compounds of the present invention can be prepared, for example, as follows.

[Preparation Method 1] Method using 6-O-methylerythromycin A as a Starting Material Step (1); 6-O-Methylerythromycin A is first reacted with an acid anhydride represented by the formula $R^4_2O$ (wherein $R^4$ is as defined above) or an acid halide represented by the formula $R^4X$ (wherein $R^4$ is as defined above, and X is a halogen atom) and a base in an inert solvent at from 0° C. to 30° C. for protection of hydroxyl groups at the 2'- and 4"-positions at the same time to give a compound represented by the formula (a):

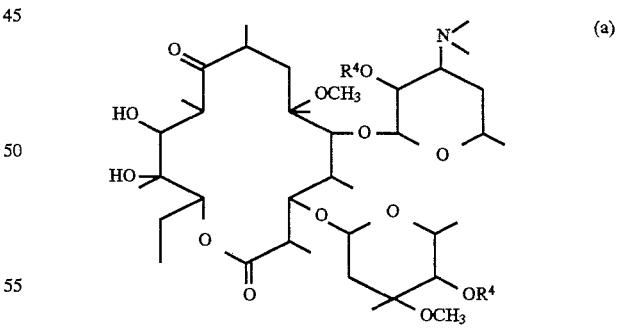

(wherein $R^4$ is as defined above). Preferable examples of the inert solvent to be used herein are dichloromethane, dichloroethane, acetone and tetrahydrofuran. The acid anhydride and acid halide to be used are those of acetic acid and propionic acid. Examples of the base to be used are pyridine and 4-dimethylaminopyridine.

Step (2); The compound (a) is reacted with 1,1'-carbonyldiimidazole and a base in a suitable solvent at room temperature to give a compound of the present invention represented by the formula (b):

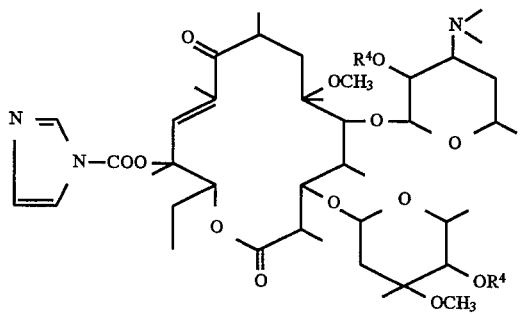

(wherein R⁴ is as defined above). Examples of the suitable solvent to be used herein are N,N-dimethyl-formamide, N-methylpyrrolidone, tetrahydrofuran, acetonitrile and a mixture thereof. Examples of the base to be used are sodium hydride, potassium hydroxide and sodium bis-trimethylsilylamide.

Step (3); The compound (b) is reacted by adding a compound represented by the formula $H_2N-C(R^1)(R^2)-CH_2-NH_2$ (wherein $R^1$ and $R^2$ are as defined above) in an inert solvent at room temperature with stirring to give a compound represented by the formula (c):

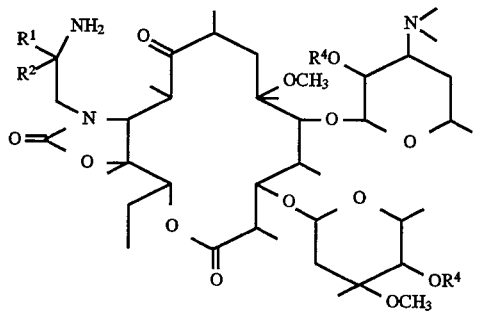

(wherein $R^1$, $R^1$ and $R^4$ are as defined above). The inert solvent to be used herein is the same as used in Step (1). The compound (c) is allowed to close a ring therein in the presence of an acid to give a compound represented by the formula (d):

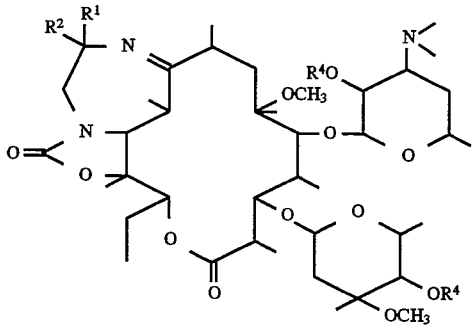

(wherein $R^1$, $R^2$ and $R^4$ are as defined above). Examples of the acid to be used herein are acetic acid and formic acid. A preferable solvent such as methanol, ethanol or toluene can be used herein, and the reaction can be accelerated by heating.

Step (4); The compound (d) is reacted with an acid to give a compound of the formula (e):

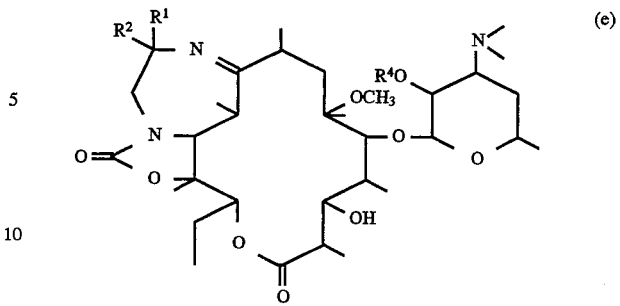

(wherein $R^1$, $R^2$ and $R^4$ are as defined above). Examples of the acid to be used herein include hydrochloric acid, hydrobromic acid and sulfuric acid, preferably 0.5 –2N hydrochloric acid, if desired, a mixture of one of these acids with a lower alcohol such as, for example, methanol or ethanol.

Step (5); The compound (e) is oxidized in an inert solvent by using chromic acid, chromic acid-pyridine, pyridinium chlorochromate, pyridinium dichromate, activated dimethyl sulfoxide and the like at –78° C. to 30° C. to give a 3-ketone form. Then, the compound is reacted in a lower alcohol or a mixture of the lower alcohol with water, if desired, by adding a base such as sodium bicarbonate, at 0° C. to 100° C., preferably room temperature to 80° C. for removal of the protective group at the 2'-position to give a compound of the present invention represented by the formula (f):

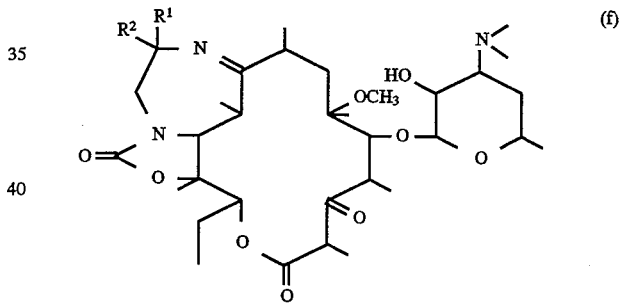

(wherein $R^1$ and $R^2$ are as defined above). The inert solvent to be used herein is the same as used in Step (1). Examples of an activating agent of dimethylsulfoxide are acetic anhydride, trifluoroacetic anhydride, oxalyl chloride, phosphorus pentachloride, pyridinium sulfate, pyridinium trifluoroacetate, 1,3-dicyclohexylcarbodiimide and 1-(3-dimethylaminopropyl)-3-ethylcarbodiimide hydrochloride. Examples of the lower alcohol to be used herein are methanol, ethanol and propyl alcohol.

[Preparation Method 2] Method Using 5-O-desosaminyl-6-O-methylerythronolide A as a Starting Material Step (6); 5-O-Desosaminyl-6-O-methyl-erythronolide A is first reacted with an acid anhydride represented by the formula $R^4_2O$ (wherein $R^4$ is as defined above) in an inert solvent, if desired, in the presence of a base such as sodium bicarbonate for protection of only the hydroxyl group at the 2'-position to give a compound represented by the formula (g):

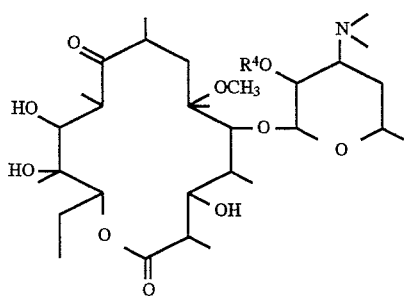

(wherein R⁴ is as defined above). The inert solvent to be used herein is the same as used in Step (1).

Step (7); The compound (g) is then reacted by using a reagent such as phosgene dimer or phosgene trimer and a base in an inert solvent under ice cooling. To the reaction mixture is added excess benzyl alcohol, the temperature of which is allowed to turn to room temperature, and stirring results in the 11,12-cyclic carbonation and benzyloxycarbonylation at the 3-position in the same vessel to give a compound of the formula (h):

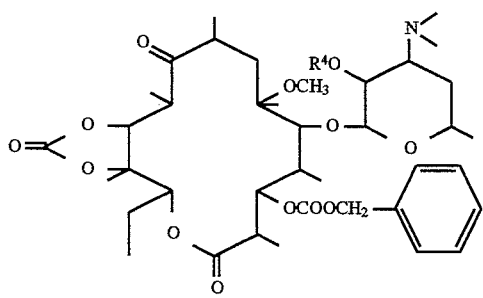

(wherein R⁴ is as defined above). The inert solvent to be used herein is the same as used in Step (1). Examples of the base to be used are pyridine, collidine, N-methylpiperidine, N-methylmorpholine, triethylamine and dimethylaniline. This compound is then reacted with 1,1'-carbonyldiimidazole and a base in a suitable solvent at room temperature to give a compound represented by the formula (i):

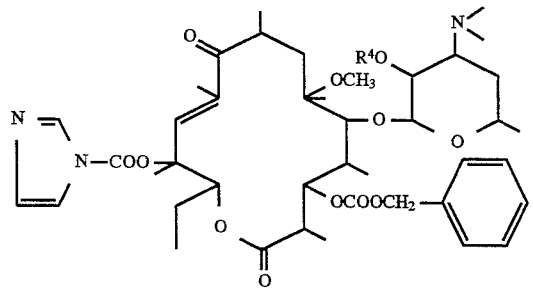

(wherein R⁴ is as defined above). The suitable solvent and the base to be used herein are the same as used in Step (2). This compound is reacted by adding a compound represented by the formula H₂N—C(R¹)(R²)—CH₂—NH₂ (wherein R¹ and R² are as defined above) in an inert solvent at room temperature with stirring to give a compound represented by the formula (j):

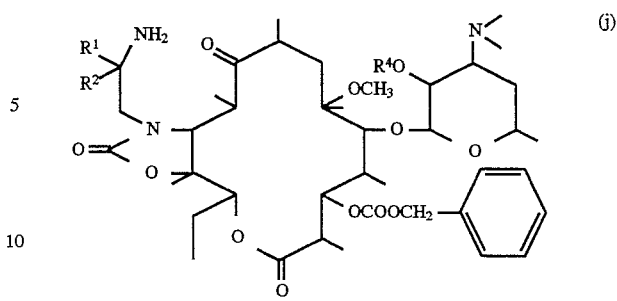

(wherein R¹, R² and R⁴ are as defined above). The inert solvent to be used herein is the same as used in Step (1).

Step (8); The compound (j) is heated in a lower alcohol to remove a protective group at the 2'-position and is allowed to close a ring therein in the presence of an acid. Then, 10% Pd-C and ammonium formate are added, followed by stirring for removal of a benzyloxycarbonyl group at the 3-position to give a compound represented by the formula (k):

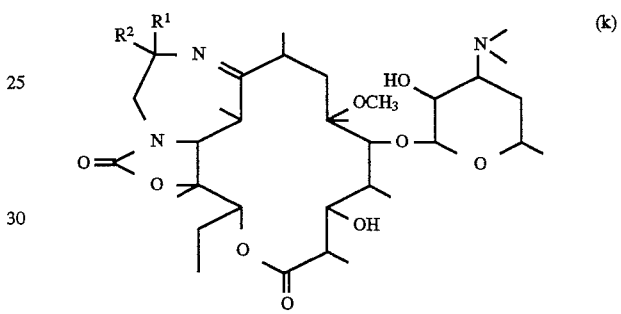

(wherein R¹ and R² are as defined above). The lower alcohol to be used herein is the same as used in Step (5), and the acid to be used herein is the same as used in Step (3).

Step (9); The compound (k) is reacted in the same manner as that of Step (6) to protect a hydroxyl group at the 2'-position, followed by the same reaction as that of Step (5) to give a compound of the present invention represented by the formula (1):

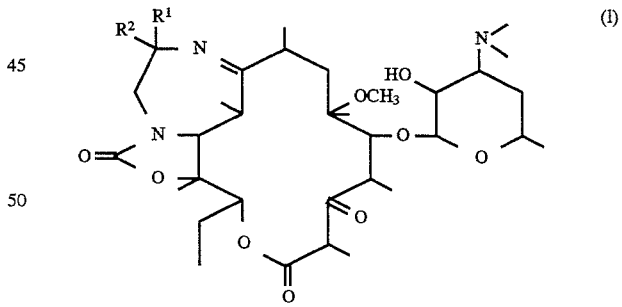

(wherein R¹ and R² are as defined above).

The compounds of the present invention can be administered orally or parenterally in the dosage form such as, for example, tablets, capsules, powders, troches, ointments, suspensions, supositories or injections, all of which can be prepared by conventional preparation techniques. The daily dose is from 1 mg/kg to 50 mg/kg, which is administered in a single dose or 2–3 divided doses.

Industrial Utilization

The compounds of the present invention have a strong antibacterial activity against erythromycinsensitive bacteria and certain resistant bacteria, and have good absorbability in the body and superior distribution in the tissue. Therefore, the compounds of the present invention are useful as antibacterial agents for the treatment of infectious diseases caused by bacteria in human beings and animals (including farm animals).

BEST MODE FOR CARRYING OUT THE INVENTION

The present invention is illustrated in more detail by the following examples.

EXAMPLE 1

Preparation of 11-amino-9-N,11-N-cyclic ethylene-9-deoxo-3,11-dideoxy-3-oxo-5-O-desosaminyl-6-O-methylerythronolide A 9-imine 11-N,12-O-cyclic carbamate Preparation Method (I)

(1) To a solution of 11.78 g (0.02 mole) 5-O-desosaminyl-6-O-methylerythronolide A in 100 ml of acetone was added 2.27 ml (0.024 mole) of acetic anhydride under ice-cooling, followed by stirring at room temperature for 6 hours. The acetone was evaporated under reduced pressure, and the residue was extracted with dichloromethane. The dichloromethane layer was washed with a saturated sodium bicarbonate solution and an aqueous sodium chloride solution successively, and dried over anhydrous magnesium sulfate. After evaporation of the solvent under reduced pressure, the residue was recrystallized from ether -n-hexane to give 12.17 g of 2'-O-acetyl-5-O-desosaminyl-6-O-methylerythronolide A as a white powder.

mp: 158~160° C.

Mass (FAB) m/z: 632 [MH]$^+$ $^1$H-NMR (200 MHz, CDCl$_3$) δ (ppm): 2.07 (3H, s), 2.26 (6H, s), 2.95 (3H, s), 3.26 (1H, s), 3.96 (1H, s)

IR (KBr, cm$^{-1}$): 3469, 1750, 1733, 1693

(2) To a solution of 42.5 g of (67.3 mmoles) of the above-mentioned compound in 230 ml of dichloro-methane was added 81.4 ml (1.01 moles) of pyridine under ice cooling. A solution of 20.2 ml (168 mmoles) of trichloromethyl-chloroformate in 20 ml of dichloromethane was added dropwise at the same temperature, and then after stirring for 3 hours 72.7 ml (673 mmoles) of benzyl alcohol was added dropwise over 30 minutes. After stirring for 16 hours at room temperature, ice pieces were added gradually, and the mixture was adjusted to pH 10 with sodium hydroxide solution. The dichloromethane was evaporated under reduced pressure, and the residue was extracted with ethyl acetate. The ethyl acetate layer was washed with a saturated aqueous sodium chloride solution and dried over anhydrous magnesium sulfate. The solvent was concentrated to 300 ml under reduced pressure. The precipitated crystals were collected by filtration to give 38.7 g of 2'-O-acetyl-3-O-benzyloxycarbonyl-5-O-desosaminyl-6-O-methylerythronolide A 11,12-cyclic carbonate.

Mass (FAB) m/z: 792 [MH]$^+$ $^1$H-NMR (300 MHz, CDCl$_3$) δ (ppm): 1.49 (3H, s), 2.07 (3H, s), 2.25 (6H, s), 2.99 (3H, s), 4.70 (1H, s), 5.21 (2H, s), 7.35 ~7.46 (5H, m)

IR (KBr, cm$^{-1}$): 1821, 1746, 1715, 1267, 1241

(3) To a solution of 10 g (12.6 mmoles) of the compound obtained in the above (2) in 100 ml of N,N-dimethylformamide - tetrahydrofuran (1:1) were added 8.18 g (50.4 mmoles) of 1,1'-carbonyldiimidazole and 1.11 g (27.8 mmoles) of 60% sodium hydride, followed by stirring at room temperature for 0.5 hour. The tetrahydrofuran was evaporated under reduced pressure, and water was poured into the residue, followed by extraction with ethyl acetate. The organic layer was washed with water and a saturated aqueous sodium chloride solution successively, and dried over anhydrous magnesium sulfate. Evaporation of the solvent gave 11.5 g of 2'-O-acetyl-10,11-anhydro-3-O-benzyloxycarbonyl-12-O-imidazolylcarbonyl-5-O-desosaminyl-6-O-methyl-erythronolide A as a white foam.

(4) To a solution of 5 g (5.9 mmoles) of the compound obtained in the above (3) in 50 ml of aceto-nitrile was added 4.0 ml (59.8 mmoles) of ethylene-diamine, followed by stirring at room temperature for an hour. After evaporation of the solvent under reduced pressure, the residue was worked up in the same manner as that of the above (3) to give 5.4 g of 2'-O-acetyl-11-(2-aminoethyl) amino-3-O-benzyloxycarbonyl-11-deoxy-5-O-desosaminyl-6-O-methylerythronolide A 11-N,12-O-cyclic carbamate.

(5) A solution of 5.4 g (6.5 mmoles) of the compound obtained in the above (4) in 50 ml of methanol was heated under reflux for an hour, the solvent was evaporated under reduced pressure, and the resulting residue was purified by silica gel column chromatography (eluent; chloroform: methanol: 25% aqueous ammonia=10:1:0.1) to give a compound deacetylated at the 2'-position. To a solution of 4.4 g (5.6 mmoles) of this compound in 40 ml of ethanol was added 0.64 ml (11.2 mmoles) of acetic acid, followed by stirring at room temperature overnight. The solvent was evaporated under reduced pressure, and 2N sodium hydroxide solution and water were added to the residue, followed by extraction with ethyl acetate. The organic layer was dried over anhydrous magnesium sulfate, and evaporated under reduced pressure. The residue was purified by silica gel column chromatography (eluent; chloroform: methanol: 25% aqueous ammonia=10:1:0.1) to give 3.66 g of 11-amino-3-O-benzyloxycarbonyl-9-N,11-N-cyclic ethylene-9-deoxo-11-deoxy-5-O-desosaminyl-6-O-methylerythronolide A 9-imine 11-N,12-O-cyclic carbamate.

(6) To a solution of 3.61 g (4.7 mmoles) of the compound obtained in the above (5) in 30 ml of methanol were added 0.72 g (20% by weight ratio) of 10% Pd-C and 2.94 g (46.7 mmoles) of ammonium formate, followed by stirring at room temperature for 45 minutes. The catalyst was filtered, the filtrate was concentrated, and 2N sodium hydroxide solution and water were added to the residue, followed by extraction with chloroform. The organic layer was worked up in the same manner as that of the above (3) to give 3.26 g of 11-amino-9-N,11-N-cyclic ethylene-9-deoxo-11-deoxy-5-O-desosaminyl-6-O-methylerythronolide A 9-imine 11-N,12-O-cyclic carbamate.

(7) To a solution of 1.9 g (3.0 mmoles) of the compound obtained in the above (6) in 20 ml of acetone was added 0.46 ml (4.9 mmoles) of acetic anhydride, followed by stirring at room temperature for an hour. The acetone was evaporated under reduced pressure, and the residue was worked up in the same manner as that of the above (3). The solvent was evaporated under reduced pressure to give 1.64 g of 2'-O-acetyl-11-amino-9-N,11-N-cyclic ethylene-9-deoxo-11-deoxy-5-O-desosaminyl-6-O-methylerythronolide A 9-imine 11-N,12-O-cyclic carbamate.

(8) To a solution of 1.64 g (2.34 mmoles) of the compound obtained in the above (7) in 16 ml of dichloro-methane were added 1.7 ml (23.4 mmoles) of dimethyl sulfoxide, 1.4 g (7.30 mmoles) of 1-(3-dimethylamino-propyl)-3-ethylcarbodiimide hydrochloride and 1.4 g (7.25 mmoles) of pyridinium trifluoroacetate, followed by stirring at room temperature for 1.5 hours. To the reaction solution were added 2N sodium hydroxide solution and water, and the mixture was extracted with dichloromethane and worked up in the same manner as that of the above (3). The solvent was evaporated, and 10 ml of methanol was added to the resulting residue, followed by heating under reflux for 2 hours. The methanol was evaporated, and the residue was purified by silica gel column chromatography (eluent; chloroform: methanol: 25% aqueous ammonia=20:1:0.1) and then crystallized from a mixture of ethyl acetate and dichloromethane to give 970 mg of the title compound.

mp: 243°–245° C.

Mass (FAB) m/z: 638 [MH]$^+$ $^1$H-NMR (300 MHz, CDCl$_3$) δ (ppm): 1.48 (3H, s), 2.26 (6H, s), 2.73 (3H, s)

$^{13}$C-NMR (75 MHz, CDCl$_3$) δ (ppm): 40.3 [3'—N(CH$_3$)$_2$], 42.4, 49.6 (NCH$_2$CH$_2$N), 49.1 (6—OCH$_3$), 156.1 (11-NCOO-12), 204.2 (C-3)

IR (KBr, cm$^{-1}$): 3411, 2938, 2778, 1759, 1737, 1712, 1650

Preparation Method (II)

(1) To a solution of 53.56 g (84.8 mmoles) of the compound obtained in the above (1) of Preparation Method (I) in 500 ml of dichloromethane was added 102.6 ml (1.27 moles) of pyridine, followed by stirring under ice cooling. A solution of 25.4 ml (212 mmoles) of trichloromethylchloroformate in 40ml of dichloromethane was added at 5°–10° C. The mixture was stirred under ice cooling for an hour and then at room temperature for 3 hours. To the reaction solution were added 50 g of ice pieces gradually, and the reaction solution was adjusted to pH 8 with a saturated sodium bicarbonate solution, and extracted with dichloromethane. The solvent was evaporated, and the resulting residue was purified by silica gel column chromatography (eluent; acetone: n-hexane: triethylamine=6-10:10:0.2) to give 41.93 g of 2'-O-acetyl-5-O-desosaminyl-6-O-methylerythronolide A 11,12-cyclic carbonate as a white foam.

$^1$H-NMR (200 MHz, CDCl$_3$) δ (ppm): 2.05 (3H, s), 2.25 (6H, s), 2.92 (3H, s), 4.57 (1H, d, J=9Hz), 4.74 (1H, s), 4.75 (1H, dd, j=10Hz, 9Hz), 5.13 (1H, dd, J=12Hz, 2Hz)

(2) To a solution of 6.04 g (9.19 mmoles) of the compound obtained in the above (1) in 80 ml of dichloromethane were added 5.285 g (27.57 mmoles) of 1-(3-dimethylaminopropyl)-3-ethylcarbodiimide hydrochloride and 7.5 ml (91.9 mmoles) of dimethyl sulfoxide. 5.326 g (27.57 mmoles) of pyridinium trifluoroacetate was added gradually, followed by stirring at room temperature for 20 hours. Additionally, 1.495 g (7.80 mmoles) of 1-(3-dimethylaminopropyl)-3-ethylcarbodidimide hydrochloride and 1.81 ml (26.00 mmoles) of dimethyl sulfoxide were added. 1.506 g (7.80 mmoles) of pyridinium trifluoro-acetate was added gradually under ice cooling, followed by stirring at room temperature for 22 hours. The reaction solution was made basic with aqueous ammonia and extracted with dichloromethane. The dichloromethane layer was washed with a saturated sodium bicarbonate solution and a saturated aqueous sodium chloride solution successively, and dried over anhydrous magnesium sulfate. The solvent was evaporated under reduced pressure, and the residue was purified by silica gel column chromatography (eluent; acetone: n-hexane: triethylamine=4:10:0.1) to give 1.62 g of a ketone form at the 3-position as a white foam. A solution of 770 mg (1.18 mmoles) of the resulting compound in a mixture of 15 ml of methanol and 10 ml of water was heated under reflux for 21 hours. The methanol was evaporated under reduced pressure, and the residue was extracted with ethyl acetate. The ethyl acetate layer was washed with a saturated sodium bicarbonate solution and a saturated aqueous sodium chloride solution successively, and dried over anhydrous magnesium sulfate. The solvent was evaporated under reduced pressure, and the crude product was purified by silica gel column chromatography (eluent; chloroform: methanol: 25% aqueous ammonia=20:1:0.1) to 350 mg of 10,11-anhydro-3-deoxy-3-deoxo-5-O-desosaminyl-6-O-methylerythronolide A as a white foam.

Mass (FAB) m/z: 570 [MH]$^+$ $^1$H-NMR (200 MHz, CDCl$_3$) δ (ppm): 2.02 (3H, s), 2.40 (6H, s), 2.92 (3H, s), 4.22 (1H, d, J=8Hz), 4.28 (1H, d, J=7Hz), 5.02 (1H, dd, J=12Hz, 3Hz), 6.64 (1H, s)

$^{13}$C-NMR (75 MHz, CDCl$_3$) δ (ppm): 40.2 [3'—N(CH$_3$)$_2$], 50.4 (6—OCH$_3$), 138.3 (C-10), 142.9 (C-11), 169.7 (C-1), 204.2 (C-3), 206.8 (C-9)

IR (KBr, cm$^{-1}$): 3436, 1747, 1712, 1669, 1458, 1380

After protection of the hydroxyl group at the 2'-position of the above-mentioned compound with an acetyl group, the reactions were carried out in the same manner as those of the above (3), (4) and (5) of Preparation Method (I), there was obtained the title compound.

Preparation Method (III)

(1) To a solution of 10 g (13.37 mmoles) of 6-O-methylerythromycin A in 30 ml of dichloromethane were added 6.00 ml (46.8 mmoles) of propionic anhydride and 0.65 g (5.35 mmoles) of 4-dimethylaminopyridine, followed by stirring at room temperature for a day. After evaporation of the solvent, the resulting residue was dissolved in ethyl acetate, washed with a saturated aqueous sodium chloride solution and a mixture of a saturated sodium bicarbonate solution and a saturated aqueous sodium chloride solution successively, and dried over anhydrous magnesium sulfate. The solvent was evaporated, and the resulting crystalline powder was recrystallized from ethyl acetate - hexane to give 8.73 g of 2', 4"-di-O-propionyl-6-O-methylerythromycin A as colorless crystals.

$^1$H-NMR (300 MHz, CDCl$_3$) δ (ppm): 1.36 (3H, s), 2.27 (6H, s), 3.01 (3H, s), 3.35 (3H, s), 4.99 (1H, d, J=5Hz), 5.07 (1H, dd, J$_1$=11Hz, J$_2$=2Hz)

$^{13}$C-NMR (75 MHz, CDCl$_3$) δ (ppm): 40.8 [3'-N(CH$_3$)$_2$], 49.3 (3"—OCH$_3$), 50.5 (6—OCH$_3$), 173.2 (—OCOEt), 173.9 (—OCOEt), 175.5 (C-1), 221.1 (C-9)

(2) To a solution of 8.35 g (9.71 mmoles) of the compound obtained in the above (1) in a mixture of 25 ml of tetrahydrofuran and 15 ml of dimethylformamide was added 4.72 g (29.1 mmoles) of 1,1'-carbonyldiimidazole. 0.58 g (14.6 nmoles) of 60% sodium hydride was added under ice cooling, followed by stirring for 5 hours. The solvent was evaporated under reduced pressure, and the residue was dissolved in ethyl acetate, washed with a saturated aqueous sodium chloride solution, and dried over anhydrous magnesium sulfate. Evaporation of the solvent under reduced pressure gave 9.13 g of 10,11-anhydro-2',4"-di-O-propionyl-12-O-imidazolylcarbonyl-6-O-methylerythromycin A as a colorless foam.

$^1$H-NMR (300 MHz, CDCl$_3$) δ (ppm): 1.78 (3H, s), 1.85 (3H, s), 2.27 (6H, s), 3.15 (3H, s), 3.34 (3H, s), 5.83 (1H, dd, J$_1$=10Hz, J$_2$=3Hz), 6.66 (1H, s), 7.07 (1H, m), 7.36 (1H, m), 8.08 (1H, m)

$^{13}$C-NMR (75 MHz, CDCl$_3$) δ (ppm): 40.7 [3'—N(CH$_3$)$_2$], 49.5 (3"—OCH$_3$), 50.8 (6—OCH$_3$), 130.9, 137.0, 137.9 (imidazole ring), 138.8 (C-10), 204.7 (C-9)

(3) Carrying out reactions by using the compound obtained in the above (2) and ethylenediamine in the same manners as those of Preparation Method (I) (4) and (5) of Example 1 successively, there was obtained the title compound.

EXAMPLE 2

Preparation of 11-amino-9-N,11-N-cyclic (1,1-dimethyl)ethylene-9-deoxo-3,11-dideoxy-3-oxo-5-O-desosaminyl-6-O-methylerythronolide A 9-imine 11-N,12-O-cyclic carbamate (1) To a solution of 6.45 g (7.7 mmoles) of the compound obtained in Preparation Method (I) (3) of Example 1 in 60 ml of acetonitrile was added 8.0 ml (76.3 moles) of 1,2-diamino-2-methylpropane, followed by stirring at 50° C. for 2 hours and then at room temperature overnight. The mixture was worked up in the same manner as that of Preparation Method (I) (4) of Example 1 to give 6.8 g of 2'-O-acetyl-11-[(2-amino- 2-methyl)propyl]amino-3-O-benzyloxycarbonyl-11-deoxy-5-O-desosaminyl-6-O-methylerythronolide A 11-N,12-O-cyclic carbamate as a white foam.

(2) 6.8 g (7.9 mmoles) of the compound obtained in the above (1) was dissolved in 60 ml of methanol, and reacted in the same manner as that of Preparation method (I) (5) of Example 1 to give 6.4 g of the compound deacetylated at the 2'-position. 6.4 g (7.8 mmoles) of this compound was dissolved in 60 ml of ethanol, and 0.89 ml (15.5 mmoles) of acetic acid was added, followed by heating under reflux for 50 hours. After reaction, the mixture was worked up in the same manner as that of Example 1 (5) to give 3.3 g of 11-amino-3-O-benzyloxy-carbonyl-9-N, 11-N-cyclic (1,1-dimethyl)ethylene-9-deoxo-11-deoxy-5-O-desosaminyl-6-O-methylerythronolide A 9-imine 11-N,12-O-cyclic carbamate.

(3) To a solution of 3.3 g (4.1 mmoles) of the compound obtained in the above (2) in 30 ml of methanol were added 660 mg of 10% Pd-C (ratio of 20% by weight) and 2.7 g (42.9 mmoles) of ammonium formate, and the mixture was reacted in the same manner as that of Preparation Method (I) (6) of Example 1 to give 2.7 g of 11-amino-9-N,11-N-cyclic (1,1-dimethyl)ethylene-9-deoxo-11-deoxy-5-O-desosaminyl-6-O-methylerythronolide A 9-imine 11-N,12-O-cyclic carbamate.

(4) To a solution of 2.7 g (4.0 mmoles) of the compound obtained in the above (3) in 30 ml of acetone was added 0.66 ml (7.0 mmoles) of acetic anhydride, and the mixture was reacted in the same manner as that of Preparation Method (I) (7) of Example 1 to give 2.5 g of 2'-O-acetyl-11-amino-9-N,11-N-cyclic (1,1-dimethyl)-ethylene-9-deoxo-1i-deoxy-5-O-desosaminyl-6-O-methylerythronolide A 9-imine 11-N,12-O-cyclic carbamate.

(5) 1.0 g (1.4 mmoles) of the compound obtained in the above (4) was dissolved in 10 ml of dichloromethane, and reacted by using 1 ml (14 mmoles) of dimethyl sulfoxide, 0.81 g (4.23 mmoles) of 1-(3-dimethylamino-propyl)-3-ethylcarbodiimide hydrochloride and 0.82 g (4.25 mmoles) of pyridinium trifluoroacetate in the same manner as that of Preparation Method (I) (8) of Example 1 to give 0.69 g of the title compound as a white foam.

Mass (FAB) m/z: 666 [MH]$^+$ $^1$H-NMR (300 MHz, CDCl$_3$) δ (ppm): 1.29 (3H, s), 1.48 (3H, s), 2.27 (6H, s), 2.70 (3H, s)

$^{13}$C-NMR (75 MHz, CDCl$_3$) δ (ppm): 40.3 [3'—N(CH$_3$)$_2$], 49.3 (6—OCH$_3$), 53.4 [NCH$_2$C(CH$_3$)$_2$N], 156.6 (11-NCOO-12), 204.0 (C-3)

IR (KBr, cm$^{-1}$): 3436, 2971, 2938, 1762, 1651

EXAMPLE 3

Preparation of 11-amino-9-N,11-N-cyclic (1-methyl)ethylene-9-deoxo-3,11-dideoxy-3-oxo-5-O-desosaminyl-6-O-methylerythronolide A 9-imine 11-N,12-O-cyclic carbamate (1) To a solution of 500 g (0.668 mole) of 6-O-methylerythromycin A in 1 L of dichloromethane were added 220.8 ml (2.34 moles) of acetic anhydride and 32.67 g (0.267 mole) of 4-dimethylaminopyridine, followed by stirring at room temperature for 2 days. The reaction solution was washed with dilute sodium hydroxide solution, and dried over anhydrous magnesium sulfate. The solvent was evaporated, and the resulting crude crystals were crystallized from ethyl acetate to give 485.2 g of 2',4"-di-O-acetyl-6-O-methylerythromycin A.

(2) To a solution of 149.77 g (0.18 mole) of the compound obtained in the above (1) in a mixture of 225 ml of N,N-dimethylformamide and 375 ml of tetrahydrofuran was added 73.08 g (0.45 mole) of 1,1'-carbonyldiimidazole. 9.37 g (0.23 mole) of 60% sodium hydride was added under ice cooling at 5°–7° C., followed by stirring for an hour. The temperature was allowed to turn to room temperature, and the reaction was carried out for 2.5 hours. Extraction with ethyl acetate gave 200.79 g of 10,11-anhydro-2',4"-di-O-acetyl-12-O-imidazolylcarbonyl-6-O-methylerythromycin A as a colorless foam.

$^1$H-NMR (300 MHz, CDCl$_3$) δ (ppm): 2.06 (3H, s), 2.12 (3H, s), 2.33 (6H, s), 3.14 (3H, s), 3.34 (3H, s), 7.07 (1H, m), 7.36 (1H, m), 8.07 (1H, m)

$^{13}$C-NMR (75 MHz, CDCl$_3$) δ (ppm): 40.6 [3'—N(CH3)2], 49.5 (3"-OCH3), 50.8 (6—OCH$_3$), 130.9, 137.0, 137.8 (imidazole ring), 138.9 (C-10), 204.6 (C-9)

(3) To a solution of 6 g (6.61 mmoles) of the compound obtained in the above (2) in 50 ml of acetonitrile was added 2.82 ml (33.1 mmoles) of 1,2-diaminopropane, followed by stirring at room temperature overnight. The mixture was worked up in the same manner as that of Preparation Method (I) (4) of the Example 1 to give 6.5 g of 11-(2-aminopropyl)amino-2',4"-di-O-acetyl-11-deoxy-6-O-methylerythromycin A 11-N,12-O-cyclic carbamate as a white foam.

(4) 6.5 g of the compound obtained in the above (3) was dissolved in 50 ml of methanol, and reacted in the same manner as that of Preparation Method (I) (5) of Example 1 to give 5.7 g of a compound removed the protective group at the 2'-position.

(5) To a solution of 5.7 g (6.54 mmoles) of the compound obtained in the above (4) in 40 ml of ethanol was added 20 ml of 2N hydrochloric acid, followed by stirring at 60° C. for 4 hours. The solution was concentrated under reduced pressure, made alkaline (pH=9) by adding 2N aqueous sodium hydroxide solution, and extracted with ethyl acetate. The organic layer was washed with water and a saturated aqueous sodium chloride solution successively, and dried over anhydrous magnesium sulfate. The solvent was evaporated under reduced pressure, and the residue was purified by silica gel column chromatography (chloroform: methanol : 25% aqueous ammonia=20:1:0.1) to give 3.9 g of 11-(2-aminopropyl) amino-11-deoxy-5-O-desosaminyl-6-O-methylerythronolide A 11-N,12-O-cyclic carbamate.

(6) To a solution of 3.9 g (5.81 mmoles) of the compound obtained in the above (5) in 40 ml of toluene was added 0.66 ml (11.5 mmoles) of acetic acid, followed by stirring at 100° C. for 3 hours. The mixture was worked up in the same manner as that of Preparation Method (I) (5) of the Example 1, and then protection of the 2'-position with an acetyl group was carried out by using 0.84 ml (8.89 mmoles) of acetic anhydride in the same manner as that of Preparation Method (I) (7) of Example 1 to give 3.0 g of 2'-O-acetyl-11-amino-9-N,11-N-cyclic (1-methyl) ethylene-9-deoxo-11-deoxy-5-O-desosaminyl-6-O-methylerythronolide A 9-imine 11-N,12-O-cyclic carbamate.

(7) 3.0 g (4.31 mmoles) of the compound obtained in the above (6) was dissolved in 30 ml of dichloro-methane, and reacted by using 6.2 ml (87.4 mmoles) of dimethyl sulfoxide, 3.16 g (16.5 mmoles) of 1-(3-dimethylaminopropyl)-3-ethylcarbodiimide hydrochloride and 5.0 g (25.9 mmoles) of pyridinium trifluoroacetate in the same manner as that of Preparation Method (I) (8) of Example 1 to give a mixture of two epimers in the cyclic ethylene moiety of the title compound. The mixture was purified by silica gel column chromatography (chloroform: methanol : 25% aqueous ammonia= 20:1:0.1) to give 1.20 g of Epimer A having low polarity and 0.76 g of Epimer B having high polarity.

Epimer A

Mass (FAB) m/z: 652 [MH]$^+$ $^1$H-NMR (300 MHz, CDCl$_3$) δ (ppm): 1.47 (3H, s), 2.29 (6H, s), 2.71 (3H, s)

$^{13}$C-NMR (75 MHz, CDCl$_3$) δ (ppm): 40.3 [3'-N(CH$_3$)$_2$], 49.0 (6—OCH$_3$), 156.1 (12—OCON—), 169.5 (C-1), 178.1 (C-9), 204.2 (C-3)

Epimer B $^1$H-NMR (300 MHz, CDCl$_3$) δ (ppm): 1.46 (3H, s), 2.28 (6H, s), 2.68 (3H, s)

EXAMPLE 4

Preparation of 11-amino-9-N,11-N-cyclic ethylene-9-deoxo-3,11-dideoxy-3-oxo-5-O-desosaminyl-erythronolide A 9-amine 11-N,12-O-cyclic carbamate To a solution of 0.76 g (1.19 mmoles) of the compound obtained in Example 1 in 60 ml of ethanol were added 0.136 ml (2.38 mmoles) of acetic acid and 300 mg (4.77 mmoles) of sodium cyanoborohydride, followed by stirring at room temperature for 15 hours. The reaction solution was neutralized with a saturated aqueous sodium bicarbonate solution, and the solvent was evaporated under reduced pressure. The residue was extracted with ethyl acetate, washed with a sodium bicarbonate solution and a saturated aqueous sodium chloride solution successively, and dried over magnesium sulfate. The solvent was evaporated under reduced pressure to give 0.68 g of a crystalline powder, which was then recrystallized from ethyl acetate to give 0.374 g of the title compound as colorless crystals.

$^1$H-NMR (300 MHz, CDCl$_3$) δ (ppm): 2.27 (6H, s), 2.90 (3H, s), 3.72 (1H, s), 3.85 (1H, q, J=7 Hz), 4.96 (1H, dd, J$_1$=11 Hz, J$_2$=2 Hz)

$^{13}$C-NMR (75 MHz, CDCl$_3$) δ (ppm): 40.3 [3'—N(CH$_3$)$_2$], 49.0 (6—OCH$_3$), 156.3 (11—NCOO-12), 169.9 (C-1), 204.0 (C-3)

EXAMPLE 5

Preparation of 11-amino-9-N,11-N-cyclic ethylene-9-deoxo-3,11-dideoxy-3-oxo-5-O-desosaminyl-erythronolide A 9-(N-methyl)amine 11-N,12-O-cyclic carbamate To a solution of 0.40 g (0.625 mmole) of the compound obtained in Example 4 in 10 ml of ethanol were added 0.11 ml (1.25 mmoles) of 35% formaldehyde solution, 157 mg (2.50 mmoles) of sodium cyanoborohydride and 0.107 ml (1.88 mmoles) of acetic acid, followed by stirring at room temperature for 15 hours. A saturated aqueous sodium bicarbonate solution was added, the solvent was evaporated, and the residue was extracted with ethyl acetate. The solvent was evaporated, and the resulting residue was purified by silica gel column chromatography (eluent; chloroform containing 4% methanol) to give 0.37 g of the title compound as a colorless foam.

Mass (FAB) m/z: 654 [MH]$^+$

Experiment (In Vitro Antibacterial Activity)

The in vitro antibacterial activity of the compound of the present invention against various experimental microorganism was measured using sensitive disc media (produced by Eiken Chemical Co.) according to the MIC measuring method specified by the Japan Chemotherpeutic Society. 6-O-Methylerythromycin A was used as a comparative drug. The results are expressed as MIC value (Minimum Inhibitory Concentration, mcg/ml), and shown in Table 1.

TABLE 1

| | In Vitro Antibacterial Activity MIC value (mcg/ml) | | |
|---|---|---|---|
| | Compound | | |
| Microorganism | Example 1 | Example 2 | Comparative drug |
| S. aureus 209P-JC | 0.025 | 0.10 | 0.05 |
| S. aureus Smith 4 | 0.10 | 0.10 | 0.10 |
| S. epidermides | 0.10 | 0.10 | 0.10 |
| II D 866 | | | |
| E. faecalis CSJ 1212 | 0.05 | 0.10 | 0.78 |
| S. aureus B1 | 0.78 | 0.20 | >100 |

We claim:

1. A 5-O-desosaminylerythronolide A derivative represented by the formula:

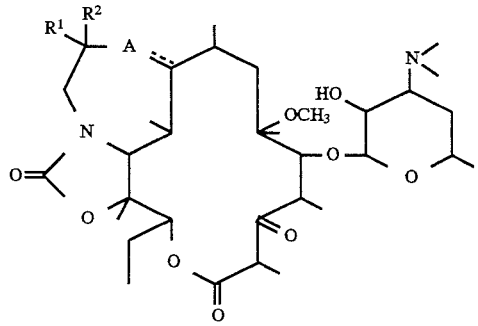

wherein -A-- is a group of —N(R$^B$)— (wherein R$^3$ is a hydrogen atom or an alkyl group having 1–3 carbon atoms) or a group represented by —N=, and R$^1$ and R$^2$ are each a hydrogen atom or an alkyl group having 1–3 carbon atoms, or a pharmaceutically acceptable acid addition salt thereof.

* * * * *

UNITED STATES PATENT AND TRADEMARK OFFICE
CERTIFICATE OF CORRECTION

PATENT NO. : 5,631,355
DATED : May 20, 1997
INVENTOR(S) : ASAKA et al

It is certified that error appears in the above-indentified patent and that said Letters Patent is hereby corrected as shown below:

Col. 11, line 8, "moles" should read --mmoles--.

Col. 12, line 22, "N(CH3)" should read --N(CH$_3$)--; and line 23, "2]" should read --$_2$]--.

Col. 14, line 52, "N(R$^B$) should read --N(R$^3$)--.

Signed and Sealed this

Sixteenth Day of June, 1998

Attest:

BRUCE LEHMAN

Attesting Officer

Commissioner of Patents and Trademarks